United States Patent [19]

Kikuta et al.

[11] Patent Number: 5,433,957
[45] Date of Patent: Jul. 18, 1995

[54] VASODILATING AGENT

[75] Inventors: Seiji Kikuta, Tanashi; Katsunori Aizawa, Okazaki; Seiji Kosemura; Tetsuro Kamiya, both of Utsunomiya; Mitsuyuki Hotta, Kaminokawa, all of Japan

[73] Assignee: Kao Corporation, Tokyo, Japan

[21] Appl. No.: 105,189

[22] Filed: Aug. 12, 1993

Related U.S. Application Data

[60] Division of Ser. No. 707,224, May 24, 1991, Pat. No. 5,288,485, which is a continuation of Ser. No. 571,877, Aug. 24, 1990, abandoned.

[30] Foreign Application Priority Data

Aug. 31, 1989 [JP] Japan .................................. 1-226212

[51] Int. Cl.⁶ .................................. A61K 7/48
[52] U.S. Cl. .................................. 424/401; 424/74; 424/195.1; 514/929
[58] Field of Search ................ 424/74, 195.1, 401, 424/74; 514/929

[56] References Cited

U.S. PATENT DOCUMENTS 4,767,618  8/1988  Grollier et al. ................ 424/74

OTHER PUBLICATIONS

CRC Handbook of Medicin or Herbs by James Duke, 1986 3rd Printing pp. 557; 242, 243.
Abstracts J 63253019 Masaki Composition for Oral Cavity.

*Primary Examiner*—Thurman K. Page
*Assistant Examiner*—Neil Levy
*Attorney, Agent, or Firm*—Oblon, Spivak, McClelland, Maier & Neustadt

[57] ABSTRACT

A vasodilating agent and a hair growth promoting agent comprising an extract of *hypericum erectum thunb* as an effective component are disclosed. The *hypericum erectum thunb* extract is prepared from ground leaf, stem, root, fruit, seed, or flower of *hypericum erectum thunb* by extraction with an organic solvent. It is effective for curing or preventing diseases caused by disorder in blood circulation such as hypertension, angina pectories, myocardial infarction, congestive heart failure, frostbite, chilblain, cold constitution, and alopecia.

3 Claims, 1 Drawing Sheet

VASODILATING AGENT

This is a division of application Ser. No. 07/707,224, filed on May 24, 1991, now U.S. Pat. No. 5,288,485 which is continuation of Ser. No. 07/571,877 filed Aug. 24, 1990, now abandoned.

BACKGROUND OF THE INVENTION

1. Field of the Invention

This invention relates to a vasodilating agent and a hair growth promoting agent, and, more particularly, to a vasodilating agent and a hair growth promoting agent comprising an extract of *hypericum erectum thunb* as an effective component.

2. Description of the Background Art

Skin diseases such as frostbite or chilblain and hair problems such as alopecia have conventionally been considered to be caused or exacerbated by insufficient blood circulation around the site of the diseases. A variety of vasodilating agents have been used in order to prevent or cure these diseases.

Many of these conventional vasodilating agents, however, involved side effects such as exanthema and tachycardia, and thus had problems from the aspect of safety.

Development of a vasodilating agent which is free from side effects and can be safely used have therefore been desired.

*Hypericum erectum thunb* has long been used as a Chinese medicine. Its whole plant has been decocted and orally administered for the purpose of hemostasis, stringency, or gargling. In folk medicine, extract of fresh leaf or stem of *hypericum erecrum thunb* is externally applied to wound, constusion, or hemorrhoid.

There has, however, been no knowledge about vasodilative action or hair growth promoting action of *hypericum erectum thunb* or its extract.

SUMMARY OF THE INVENTION

The present inventors have conducted extensive studies in order to develop a vasodilating agent exhibiting sufficient vasodilative action without side effects, and found that *hypericum erectum thunb* extracts exhibited not only a superior vasodilative action but also an excellent hair growth promoting action with little or no side effects.

Accordingly, an object of this invention is to provide a vasodilating agent and a hair growth agent comprising an extract of *hypericum erectum thunb* as an effective component.

Other and further objects, features, and advantages of the invention will appear more fully from the following description.

DETAILED DESCRIPTION OF THE INVENTION AND PREFERRED EMBODIMENTS

Figure 1:
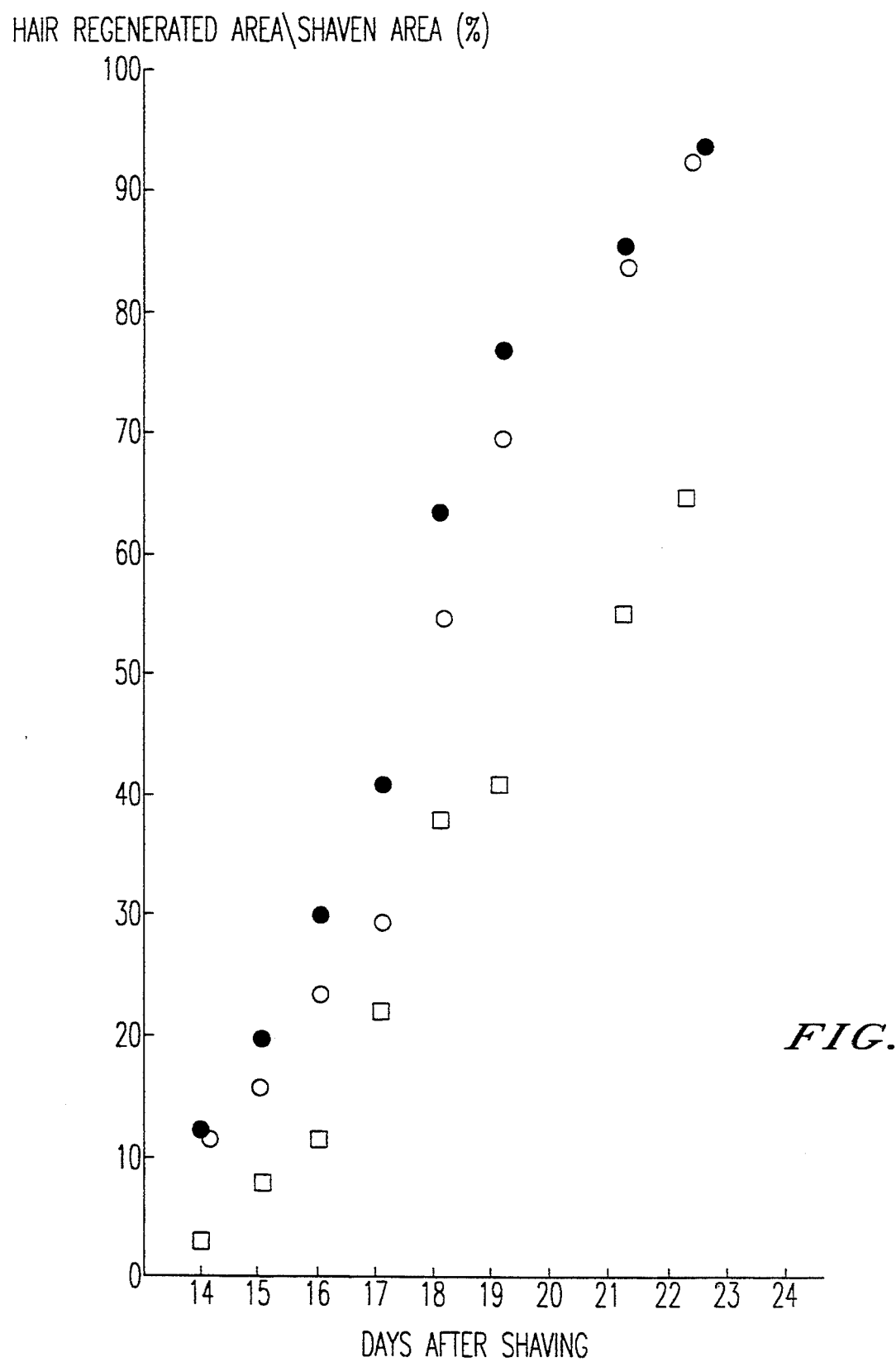
FIG. 1 is a chart showing the hair growth promoting effect of 1% and 5% solutions of the *hypericum erectum thunb* extract prepared in Reference Example 3.

The *hypericum erectum thunb* extract which is an effective component of the vasodilating agent and hair growth promoting agent of the present invention is extracted from one or more portions of *hypericum erectum thunb* selected from leaf, stem, root, fruit, seed, and flower (such portions of *hypericum erectum thunb* are hereinafter collectively referred to as the raw material). These portions, after drying or without drying, are ground and extracted with a solvent at an ambient temperature or under heating, or they are extracted using an extractor such as Soxhlet's extractor.

An organic solvent or water can be used as a solvent, with the latter being more preferable. Examples of particularly preferable organic solvents are polyhydric alcohols, e.g. glycerol, polyethylene glycol, propylene glycol; mixtures of one of these polyhydric alcohols and water, preferably 5–30% aqueous solutions of polyhydric alcohol; aqueous solutions of anionic, nonionic, or amphoteric surface active agents; alcohols, e.g. methanol, ethanol, butanol; mixtures of one of these alcohol and water, preferably 10–90%, and more preferably 20–80%, aqueous solutions of alcohol; hydrocarbons, e.g. hexane, benzene, toluene, xylene, petroleum ether; halogenated hydrocarbons, e.g. chloroform, dichloromethane, 1,2-dichloroethane; ethers, e.g. diethyl ethers, tetrahydrofuran; esters, e.g. ethyl acetate, isopropyl myristate; mineral, vegitable or animal oils, e.g. liquid paraffin, soybean oil, sesame oil; and mixtures of these mineral, vegitable or animal oils. Especially preferable solvents are hexane, acetone, petroleum ether, diethyl ether, tetrahydrofuran, chloroform, benzene, and the like.

Following processes can be given as preferable processes for the extraction.

(1) Pulverize the raw material, extract the ground material with a solvent such as hydrocarbon, aqueous lower alcohol, or the like, and evaporate the solvent from the extract.

(2) Further treat, for decoloring or the like purposes, the extract obtained in (1) above with one or more members selected from the group consisting of activated carbon, polyamide resin, polystyrene resin such as HP-20, and polyethylene methacrylate.

(3) Pulverize the raw material, extract the ground material with a solvent such as hydrocarbon, aqueous lower alcohol, or the like, and subject the extract to liquid-liquid extraction using an aqueous lower alcohol and a hydrocarbon or the like to transfer the active component to the hydrocarbon layer, followed by evaporation of the hydrocarbon solvent.

(4) Pulverize the raw material, extract the ground material with a solvent such as anhydrous or aqueous lower alcohol or the like, and subject the extract to liquid-liquid extraction using a water insoluble solvent (e.g. ethyl acetate) and water, followed by evaporation of the solvent from the organic layer or the water layer.

(5) Subject the water layer of process (4) to further liquid-liquid extraction using butanol, followed by evaporation of butanol.

(6) Treat the extract before or after the extraction of processes (4) or (5) with one or more members selected from the group consisting of activated carbon, polyamide resin, polystyrene resin such as HP-20, and polyethylene methacrylate.

(7) Pulverize the raw material, extract the ground material with a solvent, treat the extract with one or more members selected from the group consisting of activated carbon, polyamide resin, polystyrene resin such as HP-20, and polyethylene methacrylate to adsorb the active component, and extract the adsorbed active component with methanol, ethanol, acetone, or a mixture of two or more of them, followed by evaporation of the solvent.

These processes can be selected depending on the use of the target active component to be produced. For the application of the product to the hair growth promotion purpose, the *hypericum erectum thunb* extract active component obtained in the water layer of process (4), butanol layer of process (5), or the product obtained in process (7) are preferable.

The extracts produced by the above processes can be used as a vasodilating agent or a hair growth promoting agent as are or after having been fractioned by means of a suitable fractionation method such as gel filtration, silica gel column chromatography, reversed or normal phase HPLC, or the like.

The vasodilating agent or the hair growth promoting agent of the present invention can be applied either to the whole body or locally, and administered either orally or otherwise. When the extract is orally administered as a vasodilating agent or a hair growth promoting agent, it can be administered as is or after having been prepared into a suitable preparation conventionally used for oral administration for further promoting the effect of the active component. Such a preparation includes solid preparations such as tablet, pill, granule, fine particle, powder, and capsule; and liquid preparations such as emulsion, solution, suspension, syrup, elixir, and the like.

In addition to the effective component, other optional components such as inactive diluents, e.g. lactose, mannitol, fructose, hydroxypropyl cellulose, microcrystalline cellulose, starch, polyvinylpyrrolidone, aluminum magnesium methasilicate; lubricant, e.g. magnesium stearate; disintegrators, e.g. calcium gluconate cellulose; and the like can be formulated to the vasodilating agent or the hair growth promoting agent of the present invention. If required, the tablets or the pills may be coated with one or two layers of enteric coating film such as white sugar, gelatin, hydroxypropyl cellulose, hydroxypropylmethyl cellulose phthalate, or the like. Furthermore, in the case of liquid preparations, the above-mentioned inactive diluents; auxiliary agents, e.g. wetting agents, suspensions; sweeteners, flavorers, aromatics, preservatives, and the like can be incorporated in addition to the active component.

Injection is a typical non-oral administration method of the vasodilating agent or the hair growth promoting agent of the present invention. For injection, the *hypericum erectum thunb* extract is dissolved or emulsified in an aqueous medium such as injection grade purified water or physiological saline, propylene glycol, polyethylene glycol, a vegitable oil such as olive oil, alcohol such as ethanol, non-aqueous medium such as Polysolbate 80, or the like. Optional components such as preservatives, wetting agents, emulsifiers, suspension agents, and other adjuvants can be incorporated in addition to the active component into the injection formulation of the vasodilating agent or the hair growth promoting agent of the present invention. Filtration for removing bacteria, incorporation of a bactericide, or bactericidal irradiation can be used as a means for removing or destroying bacteria in the injection. Injection liquid thus prepared can be stored and dispensed at the time it is required. Alternatively, the *hypericum erectum thunb* extract which is the active component of the present invention may be prepared into a suitable sterile solid composition, which can be dissolved into a suitable sterile water or solvent for injection each time it is used.

Preparations for non-oral administration of the vasodilating agent or the hair growth promoting agent of the present invention other than injection include agents for external application in the form of liquid, ointment, lotion, tonic, spray, suspension, or emulsion; suppositories, pessaries, and the like. Especially preferable forms of the hair growth promoting agent are liquid, lotion, tonic, spray, and ointment.

The *hypericum erecrum thunb* extract of the present invention can also be prepared into tablets, powders, granules, or the like for use as a bath additive composition which can greatly promote the vasodilative effect of bathing.

In addition to the effective component, other components such as distilled water, lower alcohol, e.g. ethanol; higher alcohol, e.g. cetanol; polyhydric alcohol, e.g. polyethylene glycol, propylene glycol; cellulose, e.g. hydroxypropyl cellulose; oils and fats of animal or vegitable origin, synthetic oils and fats, petrolatum, wax, silicone, surface active agents, diluents, e.g. zinc oxide; auxiliary agents such as wetting agents, suspension agents, perfume, preservatives, and the like can be incorporated in the vasodilating agent or the hair growth promoting agent of the present invention of the form for non-oral administration.

A dose of the vasodilating agent or the hair growth promoting agent of the present invention depends on the age, weight, sex, and symptom of the subject, intended curing or treating effects, the way of the administration, the period of time of the treatment, and the like factors. A normal dose for oral administration is 1 mg to 1 g, and preferably 20 to 200 mg, as hypericum extract, for adult. It is desirable that the agent be administered 1 to several times a day. For non-oral administration an amount of 100 $\mu$g to 200 mg, preferably 1 to 10 mg, as hypericum extract, for adult is administered 1 to several times a day. For the treatment of frostbite or chilblain, a mixture containing 0.01 to 10% *hypericum erectum thunb* extract and a base component for external application medicine can be applied 1 to several times a day. For the purpose of preventing alopecia or promoting hair growth, a mixture containing 0.001 to 10% *hypericum erectum thunb* extract and a base component for external application medicine can be applied or sprayed 1 to several times a day.

Other features of the invention will become apparent in the course of the following description of the exemplary embodiments which are given for illustration of the invention and are not intended to be limiting thereof.

EXAMPLES

Reference Example 1

*Hypericum erectum thunb* (whole plant), 500 g on dry basis, was ground and 2 l of 70% aqueous solution of methanol was added to it. The mixture was heated at 50° C., shaken for 1 week, and filtered to obtain Sample 1 as the filtrate.

Reference Example 2

*Hypericum erecrum thunb* (whole plant), 500 g on dry basis, was ground and 2 l of ethanol was added to it. The mixture was dipped in the ethanol at room temperature for 1 week to extract the effective component. After evaporation of the solvent, 0.5 l of 90% aqueous methanol was added to the residue. The mixture was subjected 3 times to liquid-liquid fractionation using 0.4 l of hexane (1.21 in total). The solvent was evaporated from the hexane layer to obtain Sample 2 as the residue.

Reference Example 3

The solvent was evaporated from the 90% aqueous methanol containing the *hypericum erectum thunb* extract obtained in Reference Example 2 (before the liquid-liquid fractionation) to obtain 35.8 g of a residue. 200 ml of water was added to the residue and the mixture was subjected 3 times to liquid-liquid fractionation using 200 ml of ethyl acetate to eliminate the components transferred to ethyl acetate layer. The water layer was again subjected 3 times to liquid-liquid fractionation using 150 ml of butanol. The solvent was evaporated from the butanol layer to obtain 5.4 g of Sample 3 as a residue.

Reference Example 4

45.3 g of a residue was obtained by evaporating the solvent from Sample 1. 20.0 g of the residue was dissolved in 100 ml of 50% aqueous solution of ethanol and 4.0 g of activated charcoal was added to the mixture. After stirring for 5 hours at room temperature, the mixture was filtered, and the solvent was evaporated from the filtrate to obtain 17.0 g of a residue. 50 ml of water was added to the residue, and the mixture was passed through a column packed with 250 ml of a synthetic adsorbent (Diaion HP-20: trade name, manufactured by Mitsubishi Chemical Industries Limited) which had been conditioned with water to obtain 13.3 g of a non-adsorbed portion (Sample 4) and 2.9 g of an adsorbed portion which was eluted with methanol (Sample 5).

Reference Example 5

45.3 g of a residue was obtained by evaporating the solvent from Sample 1. 20.0 g of the residue was dissolved in 100 ml of 50% aqueous solution of ethanol and 4.0 g of activated charcoal was added to the mixture. After stirring for 5 hours at room temperature, the mixture was filtered to obtain 16.7 g of a residue. 50 ml of water was added to the residue, and the mixture was passed through a column packed with 200 ml of ion exchange resin (Amberlight IRA-400: trade name, manufactured Organo Co., Ltd.) which had been conditioned with 200 ml of water to obtain 12.5 g of a non-adsorbed portion (Sample 6).

Example 1 Vasodilative Action

<Test Method>

SD male rats, weighing 150–200 g, were anesthetized with sodium thiopental and their breasts were opened to quickly take out median arteries. After removing attached tissues with tweezers, the arteries were cut into 1–2 mm length to produce vessel fragments. The fragments were submitted to a vasodilative test according to the Magnus method using an isotonic transducer; i.e, the vessel fragments were stabilized in a nutritious physiological saline (PPS, Hepes buffer, pH 7.4) under aeration with oxygen gas for some time, following which potassium chloride was added to determine the inhibitive effect of the solution against vessel contraction caused by the addition of potassium chloride. The value was taken as the vasodilative effect of the sample solution.

<Result>

The 50% inhibitive activity concentration ($ID_{50}$) of Sample 2 for the depolarization maximum vessel contraction under a high potassium concentration (80 mM) was 11.5 μg/ml.

Example 2 House Rabbit Auricule Skin Blood Circulation

<Test Method>

Peripheral vessel expansion action of Sample 2 was measured by means of vaitalmicroscopy [Asano M. et al., *Bulletin of Institute of Public Health*, 12, 34 (1963)] using a house rabbit auricle transparent window. Six (6) male white house rabbits (weight: about 3 kg) per group, each having an acrylic chamber attached to the ear auricule, were provided to the test. According to the method of Asano [*Journal of Ethnopharmacology*, 20, 107 (1987)], 1.0 ml of a 5% ethanol solution of Sample 2 (test solution) was applied three times at 15 minutes intervals to the skin around the acrylic chamber and the changes in arteriole vessels in chamber before and after the administration were measured and compared. The results were taken as the vasodilative action of the sample.

The diameter of the arteriole vessels was measured before application of the test solution, and at 2, 4, and 8 hours after the application. The peripheral vasodilative action was compared from the average of the increase in the diameter. The results are presented in Table 1.

TABLE 1

| Test Solution | Increase in Vessel Diameter (%) | | | |
| --- | --- | --- | --- | --- |
| | Before Application | After 2 hours | After 4 hours | After 8 hours |
| Sample 2 | 100 | 111.0 | 140.0 | 145.0 |
| Ethanol | 100 | 95.0 | 94.0 | 98.0 |

The results in Table 1 demonstrate significant vasodilative action of the extract of *hypericum erectum thunb* which is the effective component of the vasodilating agent of the present invention. In particular, remarkable enhancement of the blood circulation bagan 4 hours after the application, while exhibiting orderly turbulence in the vessel motion, and this effect was maintained at 8 hours after the application of the sample.

Example 3 Hair Growth Promoting Action

<Test Method>

Backs of 20 C3H/HeNCrj mice (age: 49 days) per group were shaven with an electric hair-clipper and an electric shaver so as not to damage the skin. Starting from the next following day, a 1% solution or 5% solution of Sample 3 containing α-monoisostearylgryceryl ether as a base solvent was applied to the shaven portions one time a day. Image analysis was performed on photographs of the mouse backs to measure the shaven area and the area in which the hair regenerated. The ratio of the areas was taken as the hair growth promoting action.

<Results>

The results are given in FIG. 1, in which solid and open circles indicate the values obtained by the application of the 5% solution of Sample 3 and the 3% solution of Sample 3, respectively, and open squares are those of control group. The Figure demonstrates significant hair growth promoting effects in the groups to which 1% or 5% solution of Sample 3 was applied, especially starting from 19th day after the application, as compared with the control group.

Example 4 Acute Toxicity Test

No fatal problems were found in mice to which 10 g/kg of Sample 1 was orally administered. Accordingly, it is concluded that the extract of *hypericum erectum thunb* which is the effective component of the vasodilating agent and the hair growth promoting agent of the present invention is extremely safe.

Example 5 Bath Additive Composition

A bath additive preparation in the form of tablets, 50 g each, was prepared from a mixture of sodium bicarbonate (42%), sodium carbonate (15%), Sample 1 (1.8%), dextrin (0.8%), and a perfume (0.4%). The tablets gave a favorable warming effect during and after bathing.

Although the active component of the extract of *hypericum erectum thunb* which is the effective component of the vasodilating agent and the hair growth promoting agent of the present invention is yet to be identified, it can be extracted and concentrated by the method of the present invention and exhibits remarkable vasodilating action. It is effective for curing or preventing diseases caused by disorder in blood circulation such as hypertension, angina pectories, myocardial infarction, congestive heart failure, frostbite, chilblain, cold constitution, alopecia, and the like.

Obviously, numerous modifications and variations of the present invention are possible in light of the above teachings. It is therefore to be understood that within the scope of the appended claims, the invention may be practiced otherwise than as specifically described herein.

What is claimed is:

1. A method of promoting vasodilation in a subject in need of the same, comprising applying to the skin of said subject an amount of an agent effective to promote vasodilation in said subject, said agent consisting essentially of, as an active agent, an extract of *hypericum erectum thunb*, in a pharmacologically acceptable carrier.

2. The method of claim 1, wherein said extract is extracted from one or more portions of *hypericum erectum thunb* selected from the group consisting of leaf, stem, root, fruit, seed and flower.

3. The method of claim 1, wherein said extract is obtained by extraction with an organic solvent.

* * * * *